United States Patent [19]

Coutarel

[11] 4,001,585
[45] Jan. 4, 1977

[54] SAMPLE CONVEYORS
[75] Inventor: Yves Coutarel, Montrouge, France
[73] Assignee: Intertechnique, Plaisir, France
[22] Filed: July 1, 1975
[21] Appl. No.: 592,328
[30] Foreign Application Priority Data
　　July 5, 1974　France .............................. 74.23518
[52] U.S. Cl. ................................. 250/328; 214/310
[51] Int. Cl.² ..................... G01T 1/00; B65G 65/00
[58] Field of Search ..................... 250/328; 214/310
[56] References Cited
UNITED STATES PATENTS 3,270,202　8/1966　Long et al. ........................ 250/328
3,654,472　4/1972　Hof et al. ....................... 250/328 X
3,855,473　12/1974　Burgess et al. ..................... 250/328

*Primary Examiner*—Archie R. Borchelt

[57] ABSTRACT

A sample conveyor for a liquid scintillation spectrometer or gamma counting system comprises a plurality of cassette carriers and a mechanism for moving the carriers step by step along a closed path which includes a transfer station. Each carrier has an open bottom and may receive a cassette whose bottom wall consists of lips which may be opened by a mechanism when the corresponding location is at the transfer station.

15 Claims, 7 Drawing Figures

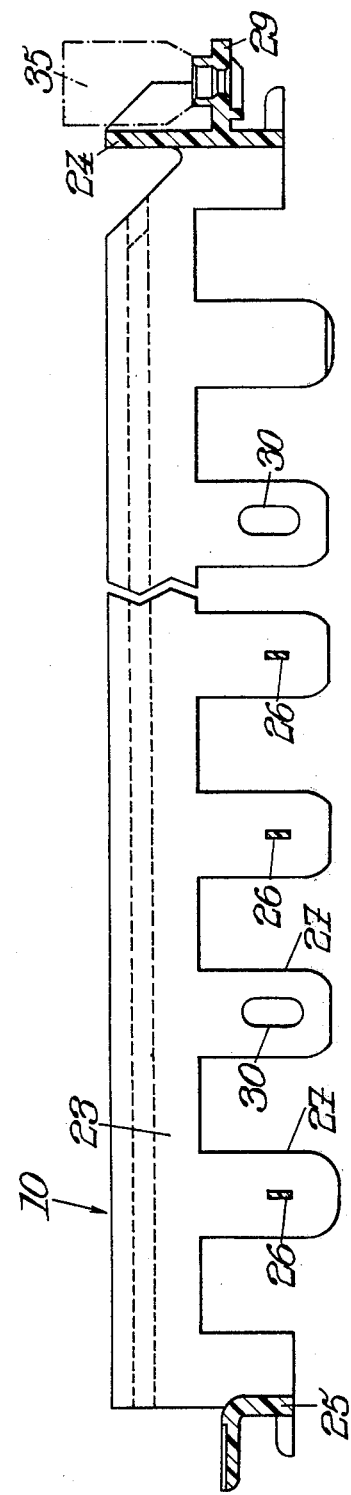

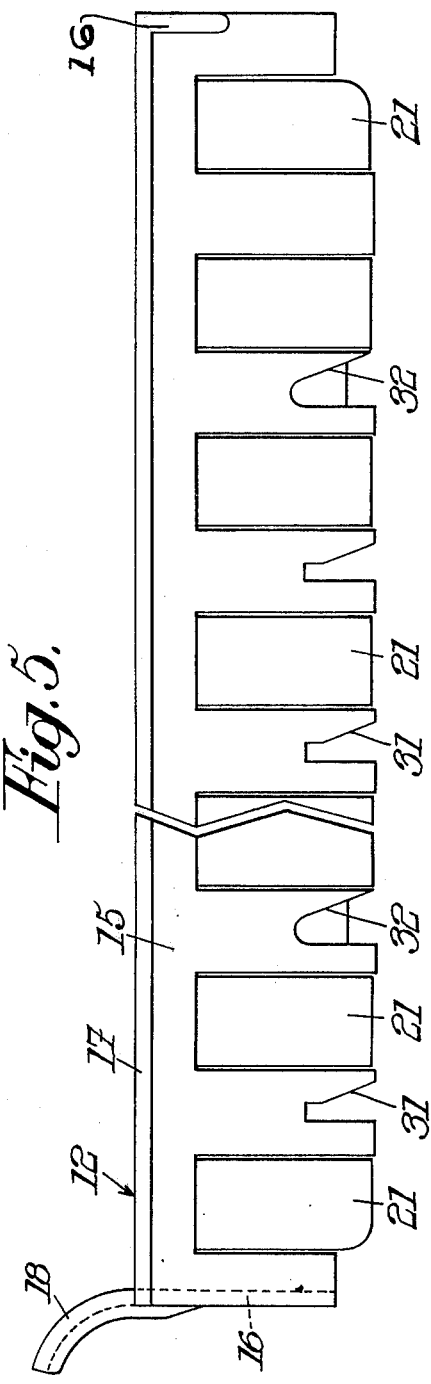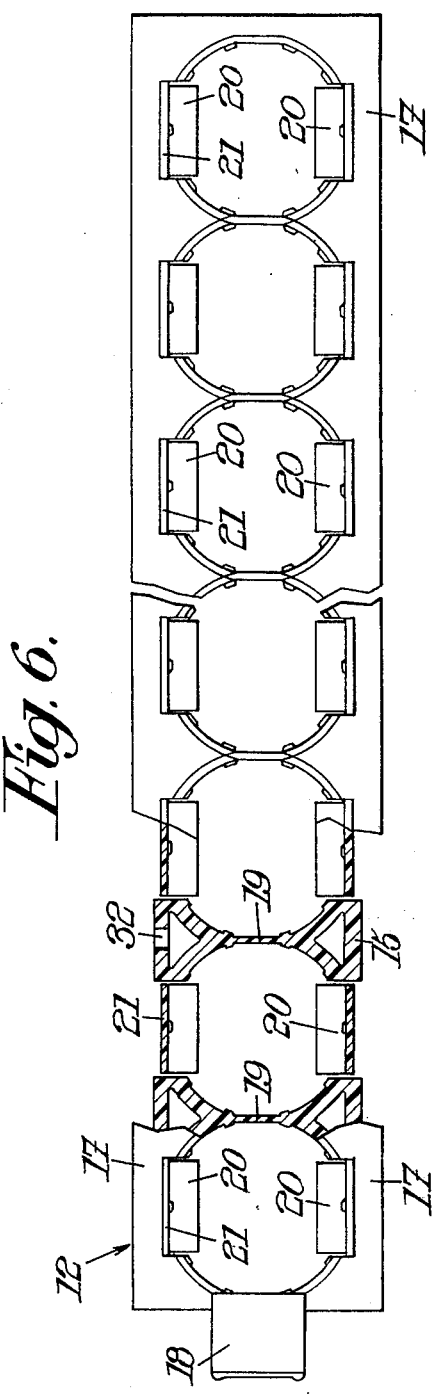

SAMPLE CONVEYORS

BACKGROUND OF THE DISCLOSURE

This invention relates to sample conveyors for measuring systems, more particularly to sample conveyors suitable for use in systems for making repeatitive measurements on a large number of consecutive samples; it also relates to individual components of such conveyors and in particular to cassettes for receiving a plurality of samples and enabling the same to be handled en bloc.

An important but not exclusive use of the invention is in systems for counting the radio-activity of samples in test tubes or vials. Most present art liquid scintillation counters use automatic sample changers comprising a sample conveying chain conveyor. All the samples loaded in the conveyor are brought consecutively to an elevator which moves down the sample to a counting station where its activity is determined and then returns the sample to the same link of the conveyor. Automatic sample changers of this kind are simple and reliable but their capacity is limited to the number of links in the conveyor, they are bulky and the samples must be placed in the chain links one at a time.

Another prior art automatic sample changer comprises trays or racks into which samples can be placed outside the apparatus, the trays or racks then being placed in the changer. A mechanism which is much more complex and slower than the conventional elevator system is then needed to transfer the samples to the counting station.

SUMMARY OF THE INVENTION

It is an object of the invention to provide a sample conveyor for measuring systems which improves upon the prior art devices and has the advantages of the tray or rack systems while making it possible to retain an elevator system.

According to an aspect of the invention, there is provided a sample conveyor for a measuring system, comprising: a plurality of cassettes each provided with sample receiving locations distributed regularly in the cassette and each having mechanical means for supporting a sample at each said location; means for moving said cassette consecutively and stepwise along a closed path for sequentially bringing said locations to a transfer station; and means at said transfer station for forcibly opening said mechanical means so that the sample in said cassette can be moved out of the cassette.

The means for mechanically supporting a sample typically consists of bottom wall means. Such bottom wall means may be in the form of a pair of confronting lips at each sample receiving location. The sample is of such size as to be supported by the lips when the latter are in released condition. The system includes a mechanism which, when operated, spreads apart the lips. That mechanism may be constituted by a stationary ramp which cams out the lips when the corresponding location is moved to the transfer station. It may also comprise movable fingers adapted to separate the lips from one another for the time necessary for the sample to be moved across the lips in the upward or downward direction. The advantage of the mechanism including movable fingers over a ramp is that friction is less important and the lips are stressed only for the time necessary for passage of the sample. The lips are for instance carried by vertical resilient legs which tend to restore the lips to their sample retaining position.

The invention will be better understood from the following description of a conveyor which is a non-limitative embodiment of the invention. The description refers to the accompanying drawings.

SHORT DESCRIPTION OF THE DRAWINGS

FIG. 4 shows the front and rear portions of a cassette carrier in section along its longitudinal centre plane;

FIG. 5 is a view in elevation of the terminal parts of cassette adapted to be received in the carrier of FIG. 4;

FIG. 6 is a view on an enlarged scale of one of the terminal parts of the cassette of FIG. 5, the view being partly a plan view and partly a mid-height section;

DESCRIPTION OF PREFERRED EMBODIMENTS

Figure 1:
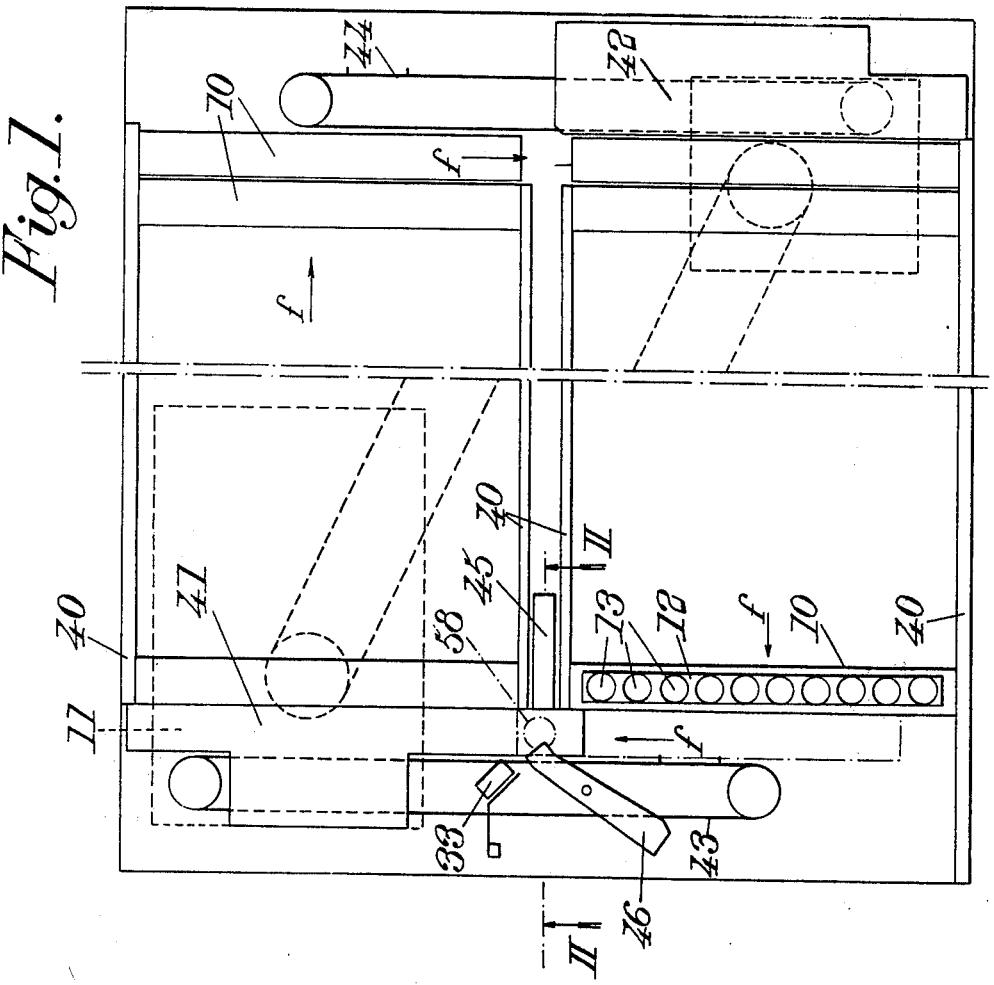
FIG. 1 is a very diagrammatic plan view showing how the cassette carriers are arranged in a conveyor which brings samples to a counting station in sequence.

Referring to FIG. 1, there is shown the general layout of the conveyor. The conveyor has a plate and a predetermined number of cassette carriers 10 which are arranged to be moved on the plate along a planar path indicated by arrows $f$. The plate has slide ways 40 which retain the carriers 10 located in two parallel rows on either side of a mid plane of the plate. The space behind the last carrier of each row forms a passage 11 via which the first carrier of each row can be moved to the back of the other row. Means including two pushers 41 and 42 or the like are provided for advancing each row by steps equal to the width of a carrier. The system also includes means for advancing the first carrier of each row stepwise to the back of the other row. Such means includes endless belts 43 and 44 having projecting pins for engagement with the carriers.

Each carrier is adapted to receive a cassette 12. A single cassette 12 is shown diagrammatically in FIG. 1. That cassette has $n$ sample receiving locations. Each sample consists of a bottle or vial containing a liquid solution if the system is a liquid scintillation spectrometer. Each sample 13 is separated from the adjacent sample by a distance equal either to the incremental movement or step of the carrier 10 or to an integral multiple of such step.

A counting system (not shown) is associated with and disposed below the plate. A transfer mechanism is provided for bringing a sample vial retained by the carrier at the transfer station from the cassette 12 to a counting station, then for returning it to its initial position.

The transfer mechanism comprises an elevator which can be of the type disclosed in U.S. Pat. No. 3,809,897 assigned to the assignee of this invention and to which reference may be had. The platform 14 of the elevator which supports the sample vial during its upward and downward movements, has been shown in FIGS. 2 and 3.

The cassettes 12 have a base or bottom wall for retaining the vials while the cassettes are handled or are moved on the plate and for allowing the vials to pass through so that they can be transferred to the counting station.

Figure 2:
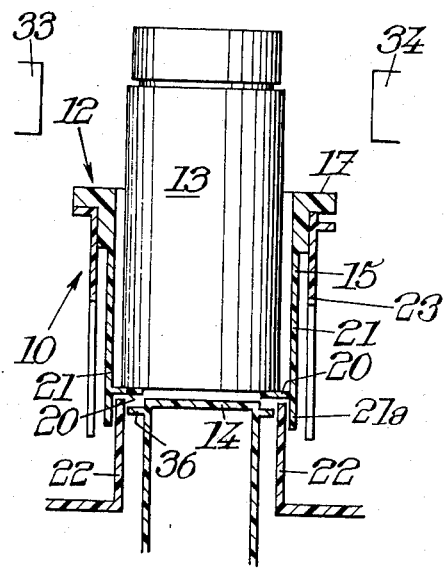
FIGS. 2 and 3 are very diagrammatic views of the relative arrangement of a cassette carrier, a cassette, a vial and a transfer elevator in vertical section along line II—II of FIG. 1, with the bottom wall of the cassette open and closed, respectively.
Figure 3:
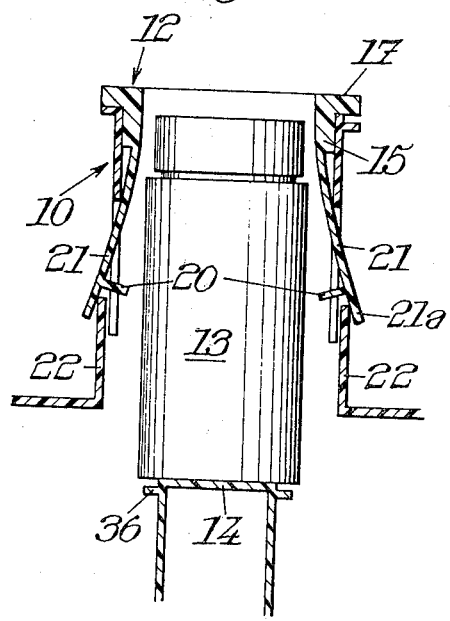

The cassette which is shown diagrammatically in FIGS. 2 and 3 and partially in FIGS. 5 and 6 consists of a molded part of a slightly resilient material, typically plastics material. The cassette frame has lateral vertical walls 15 and vertical end walls 16. The lateral walls 15 have flangers 17 adapted to be supported by the carrier 10. The cassettes can be positioned and removed by means of a handle 18. The lateral walls of the cassette are interconnected by integral molded transverse partitions 19 separating chambers or locations for receiving vials 13, there being e.g. 10 such chambers or locations. In the embodiment shown, each vial receiving chamber has a bottom wall adapted to be opened independently of the bottom wall of the other chambers; the bottom wall consists of two lips 20 which project transversely inwardly from two legs 21 integral with the upper portion of the cassette 12, which is thicker than the leg and constitutes the frame. Each leg 21 is formed below the lip 20 with a projection 21b which enables a finger 22 at the transfer station to move the leg 21 outwardly far enough for the vial to pass through the lips 20 (FIG.3).

Figure 7:
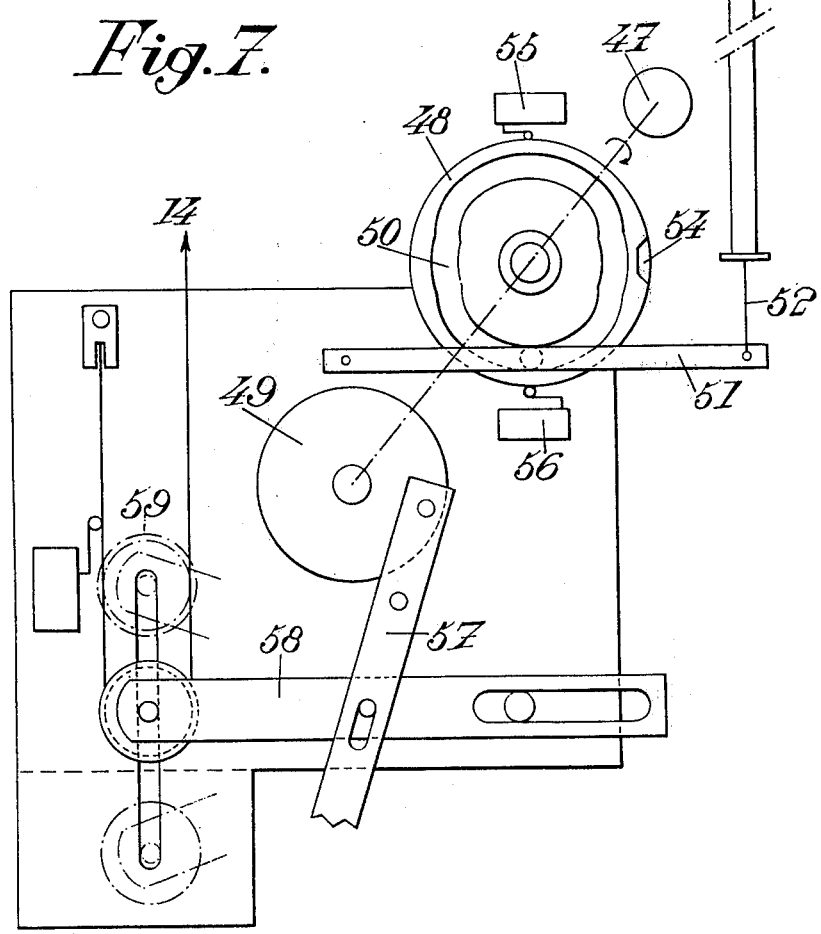
FIG. 7 is a sketch indicating the operative connections between the mechanism for opening the bottom walls of the cassettes and the sample elevator.

A mechanism for actuating the fingers 22 and the elevator in time relation is illustrated in simplified and diagrammatic form on FIG. 7. It includes a motor 47 whose shaft carries a rotating cam 48 and a disk 49.

The cam 48 is formed with a groove 50 which retains a roller carried by a lever 51 connected by a flexible web or wire 52 to a toggle 53 which moves the finger 22 from the position illustrated in solid line to the position illustrated in dash-dot line upon a 90° rotation of cam 48. The cam is also formed with a notch 54 cooperating with switches 55 and 56 which are closed except when confronting the notch and are serially mounted in an energization circuit of motor 47.

A lever 57 is pivotally connected with disk 49 and controls the platform 14 via a linkage which need not be described since it may be quite similar to that described in U.S. Pat. No. 3,809,897.

Referring to FIG. 4, there is shown a carrier 10 having a frame whose lateral walls 23 are interconnected at one end by a cross-partition 24 which extends over most of the height of the carrier 10 and at the other end by a partition 25 appreciably lower. The bottom wall of the carrier 10 is open; however, for increased rigidity, the lateral walls 23 are interconnected by horizontal ribs 26. The carrier 10 is so shaped that the legs 24 of the cassette 12 in the carrier can be bent apart from one another; to use the available space more efficiently the lateral walls 23 are cut to leave castellations 27 opposite the positions of the legs. The transverse dimension of the carriers can therefore be only slightly greater than the transverse dimension of the cassettes.

The carriers are associated with means for guiding them onto the plate and for driving them stepwise. Referring to FIG. 4, the end walls 24, 25 of each carrier have two flanges which straddle the slideways 40 of the plate during the movement of the carriers 10 in the rows. The top flange 29 of the rear wall 24 is formed with a recess aperture adapted to receive a programming plug giving automatic determination of the parameters of the required measurements. Such plug can be e.g. of the type disclosed in U.S. Pat. No. 3,749,916 assigned to the assignee of the present invention, or in French Patent Application No. 74.23515.

For the stepwise drive of the carriers near the transfer station, the lateral walls 23 are formed with slots 30 engageable by the pins of the drive belts 43, 44. The slots 30 are distributed at equal spacings and there are e.g. three slots in each lateral wall. The cassette is so designed as not to interfere with the engagement of the pins and to allow the connecting ribs 26 to pass; accordingly, the cassette shown in FIGS. 5 and 6 is formed with straight-walled recesses 31, for association with the ribs 26, and with wider slots 32 which extend beyond the slots 30.

The carrier shown in FIG. 4 can receive not only cassettes of the kind shown in FIGS. 5 and 6 (such cassettes taking up the entire width of such carrier) but also cassettes for samples having a smaller transverse size. Of course, it would be possible to provide cassettes in which samples contained in narrow vials or list tubes are distributed at the same interval, but then the capacity of the system would not be fully used. To obviate this disadvantage, cassettes other than the regular cassettes shown in FIGS. 5 and 6 can be provided in which the sample-receiving locations are distributed at intervals representing a fraction (generally one-half) of the interval between the sample-receiving locations in the regular cassette. In this case, if the mechanism for driving the carriers is designed to optionally move them by increments of half a normal step, the capacity can be almost doubled (19 half-diameter sample bottles being accomodated in one carrier). A sample identification probe 46 is then provided (FIG. 1). The ribs 26 of the carrier shown in FIG. 4 are such that modified cassettes of the type just described can be used, since the ribs 26, which are in positions where they do not exhibit the passage of the sample bottles, are of reduced longitudinal size. The program plug 35 carried by the rear cross-wall 24 of the carrier can as well carry a coded indication for a sensor to determine whether the arriving carrier contains a standard 10-sample cassette or a 19-sample cassette.

Carriers compatible with several types of cassettes (the samples being disposed at different intervals according to the type of cassettes) may be used as well when the samples are removed otherwise than through the bottom of the cassette. Compatibility is even easier in the case of upwards removal by grippers which engage with the neck of a vial, test-tube or test-tube container of any diameter in the cassette.

Since the operation of the facility hereinbefore described is apparent from the foregoing description, it will merely be summarized, assuming that all the carriers 10 contain standard cassettes of the kind shown in FIGS. 5 and 6. No reference will be made to the mechanisms for moving the rows of loaders since there are many known mechanisms of such a kind, nor will there be any reference to means for carrier identification. It is sufficient to note that the carriers may be numbered sequentially, e.g. from 1 to 40. An identification mark on the carrier numbered 1 serves to reset a counter whenever that carrier passes by the counting station, and the counter subsequently gives a continuous display of the number of the cassette carriers present at the transfer station.

Assuming that the carriers are initially grouped in two complete rows, with the carriers of the upper row in the position illustrated in FIG. 1 and the carriers of the lower row moved by one step to the left, the stepwise belt 43 for the carrier of the lower row operates and in a first phase brings the first sample location 13 opposite the transfer station 58 (as shown in dash-dot lines in FIG. 1). If a detector system at the transfer station, for instance, including a light emitter 33, and a detector 34 detects the presence of a sample, an operating sequence of the transfer mechanism is initiated.

In initial condition, cam 48 is an angular position for which switch 55 confronts notch 54 and is open while switch 56 is closed. When the motor is energized by a separate circuit, cam 48 rotates and switch 55 closes thereby maintaining energization of motor 47. During initial rotation of the motor and cam, lever 51 is moved angularly and drives the fingers 22 apart. The sample then rests onto the platform 14. For that time period, disk 49 is also rotated and drives lever 57 which takes up the lost motion of its connection with a second lever without moving the wheel 59 which remains in its upper position (in dash-dot line on FIG. 7). Continuing movement of motor 47 retains the fingers 22 in spaced conditions and causes downward movement of wheel 59. When the cam 48 has moved by 180° from its initial position, switch 56 opens and the motor stops. During the final portion of the angular motion of the cam, the fingers 22 move back and release the legs of the cassette which return to their rest condition.

The sample is then counted under conditions (e.g. precount, pretime, width of energy windows . . . ) which may be automatically adjusted in response to the information read from the plug 35 (FIG. 4).

After the counting operation has been completed, motor 47 is energized again. Cam 48 rotates and closes switch 56. The fingers 22 are moved apart while the platform 14 lifts back the sample to the cassette to a level above the lips 20. Last the lips close and switch 55 opens. The platform 14 can have a flange-like edge 36 which determines the appropriate height by bearing on an abutment.

The belt mechanism then moves the carrier on by one step and the same sequence is repeated.

The invention therefore provides a sample conveyor which is very convenient to use since prefilled cassettes can be substituted rapidly and conveniently into captive cassette carriers for other cassettes. None of the advantages of conventional elevator mechanism is lost. The conveyor is very flexible since it is adaptable to samples of different kinds and transverse sizes, with optimum use of available capacity.

I claim:

1. A sample conveyor for a measuring system, comprising: a plurality of cassettes each provided with sample receiving locations distributed regularly in the cassette and each having mechanical means for supporting a sample at each said location; means for moving said cassettes consecutively and stepwise along a closed path for sequentially bringing said locations opposite a transfer station; and means at said transfer station for forcibly opening said mechanical means so that the sample in said cassette can be moved out of the cassette.

2. A conveyor according to claim 1, having a plurality of open-bottom cassette carriers each constructed to receive one cassette, wherein said moving means are constructed to move said carriers stepwise on a stationary horizontal plate.

3. A conveyor according to claim 1, wherein said mechanical means comprises bottom wall means supporting said samples, said wall means being closed in released condition and constructed to be forcibly opened by said means at the transfer station.

4. A conveyor according to claim 3, wherein said bottom wall means consist of transversal lips projecting inwardly from resiliently deformable fingers connected to a rigid cassette frame and which can be spread apart from each other by said means at the transfer station.

5. A conveyor according to claim 4, wherein said means at the transfer station comprise fingers movable between a rest position in which their spacing is smaller than the spacing of said fingers in released condition and an actuating position in which their spacing is increased.

6. A conveyor according to claim 5, having means for actuating said fingers in time relation with the actuation of a lift mechanism supporting the sample when the latter is released from the lips.

7. A conveyor according to claim 1, including means associated with each said cassette for receiving a programming plug and means for reading coded data on the plug of the next cassette to be brought to said transfer station and for automatically programming the measuring system responsive to the data coded on the programming plug.

8. A conveyor according to claim 2, wherein said means for moving the cassette carriers are controllable for the steps to be adjustable at different values, all said values but one being multiples of the value of the last step.

9. In a conveyor having a number of cassette carriers and means for moving said carriers stepwise along a closed path including a transfer station, a cassette provided with a plurality of locations regularly distributed in a row along the direction of movement of the cassette at the transfer station when located in one said carrier, said cassette having bottom wall means at each said location, said wall means in rest condition being constructed to support a corresponding sample in said cassette and being arranged for being forcibly openable for releasing the sample.

10. A cassette according to claim 9, wherein said bottom wall means comprises two horizontal lateral lips carried by respective resilient vertical legs projecting downwardly from a rigid cassette frame and integral with the latter.

11. A conveyor according to claim 10, wherein the lips have downward projections beyond the lips adapted to cooperate with means for forcibly opening said legs.

12. A sample conveyor for an automatic radioactivity measuring system, comprising a plurality of cassette carriers, means for moving said carriers consecutively along a closed path passing at a transfer station, each carrier being constructed to receive a cassette having sample receiving locations distributed at equal intervals in a row, said carrier being constructed to receive a plurality of different types of cassettes having different spacings between said locations, all said spacings being multiples from each other, and said means for moving the carriers being constructed to optionally move said carriers past the transfer station with steps equal to anyone of said spacings.

13. A conveyor according to claim 12, wherein each said carrier is constructed to receive a removable plug indicating the spacing between the locations of the cassettes carried by the carrier, and means are provided for sensing said plug and adjusting said step responsive to the indication given by said plug.

14. A conveyor according to claim 1, wherein said mechanical means comprises resiliently deformable fingers means at each said location and said finger means being formed with transversal lip means for retaining a sample at said location.

15. A sample conveyor according to claim 1 wherein each said cassette is a one-piece molding of plastic material and wherein said mechanical means comprises a plurality of fingers, each having an end connected to a rigid part of the cassette and another end formed with an inwardly directed transverse lip, said lip so-dimensioned that it projects into the space limited by said rigid portion when said finger is in a released condition for retaining one of said samples, said means and said transfer station being constructed for resiliently flexing said fingers by an amount sufficient for the lips thereof to release the corresponding samples.

* * * * *